United States Patent [19]

Kupers et al.

[11] Patent Number: 4,701,421

[45] Date of Patent: Oct. 20, 1987

[54] DETERMINATION OF PROTECTING ANTI-HBV IMMUNOGLOBULINS

[75] Inventors: Leonardus P. C. Kupers, Jv Oss; Ludovicus F. T. Matthyssen, Ed Oss, both of Netherlands

[73] Assignee: Akzo, N.V., Arnhem, Netherlands

[21] Appl. No.: 644,440

[22] Filed: Aug. 27, 1984

[51] Int. Cl.$^4$ ................. G01N 33/543; G01N 33/569; A61K 39/29

[52] U.S. Cl. ......................................... 436/518; 435/7; 435/28; 436/531; 436/544; 436/545; 436/546; 436/800; 436/809; 436/819; 436/820; 424/89

[58] Field of Search ...................... 435/7, 28; 436/531, 436/544, 546, 545, 800, 809, 819, 820, 518; 424/89

[56] References Cited

U.S. PATENT DOCUMENTS 4,197,361  4/1980  Hoff ................................... 436/820

FOREIGN PATENT DOCUMENTS 2051357  1/1981  United Kingdom .

OTHER PUBLICATIONS

Hoofnagle, Gastroenterology 72, p. 290-296, 1977.
Shenertz, New England J. Med. 309, p. 1519, 1983.
Swenson, J. Clinical Microbiology 18(2), p. 305-309, 1983.
L. Matthyssen et al., A Sandwich Enzyme-Immunoassay for Antibodies Against the "A"-Deferminant of HBsAg Using Monoclonal Subtype-Specific Enzyme Labelled Antibodies, Abstract, Symposium of the European Society Against Virus Research, Clermont-Ferrand, France, Sep. 12 to 15, 1983.

*Primary Examiner*—Robert J. Warden
*Assistant Examiner*—Robert Benson
*Attorney, Agent, or Firm*—Wegner & Bretschneider

[57] ABSTRACT

A novel method for the determination of protecting anti-HBV immunoglobulins is based on the use of two different HBsAg reagents: one insolubilized and having the antigenic type AX and one labelled and having the antigenic type AY, wherein A represents the epitope or epitopes which are common to all HBsAg serotyes, wherein X and Y both represent combinations of the epitopes which are not common to all HBsAg serotypes, and where the combinations X and Y have no epitopes in common.

22 Claims, No Drawings

DETERMINATION OF PROTECTING ANTI-HBV IMMUNOGLOBULINS

The present invention concerns a method for the determination of immunoglobulins which give protection against hepatitis B virus (HBV) infection, and test kits for use with this method.

Transmission of HBV generally occurs with blood or blood products. Apart from the patients treated with blood or blood products, also the persons handling these products and persons handling HBV-infected patients are threatened by HBV infections. These and other high risk groups increasingly often are vaccinated against HBV infection. Vaccines against HBV, however, are very expensive. Prior to vaccination a prescreening of immunoglobulins giving protection against HBV infection is generally carried out and persons already having immunity against HBV are selected.

For this prescreening generally use is made of a method comprising incubating the immunoglobulins to be detected with hepatitis B surface antigen (HBsAg) bound to a solid support and HBsAg bound to a marker, whereby the presence of immunoglobulins directed against HBsAg (anti-HBs) is indicated by the binding of the marker to the solid support.

Persons selected by this method to be immune occasionally may not possess full protection against subsequent HBV infections. Several authors reported reinfection of chronic HBV carriers with HBV of a different serotype (R. J. Sherertz et al., New England J. Med. 309, 1519, 1983; P. D. Swenson et al., J. Clin. Microbiol. 18, 305–309, 1983), hence the presence of antibodies against HBsAg per se may not always indicate immunity to HBV infection.

The aim of the present invention therefore is to furnish a method which unequivocally indicates the presence and/or the amount of immunoglobulins, which provide full protection against HBV infections.

The method according to the invention comprises incubation of the immunoglobulins to be determined with insolubilized HBsAg of the antigenic type AX and with HBsAg of the antigenic type AZ, wherein A represents one or more epitopes common to all HBsAg types, and X and Z both represent a combination of the epitopes which are variable and not common to all HBsAg types, and wherein furthermore said combinations X and Z do not contain epitopes in common, wherein said HBsAg of the antigenic type AZ is or has been labeled, whereafter the binding of the label to the insolubilized phase is qualitatively or quantitatively determined.

With A is meant any antigenic site common to all of the hepatitis B virus variants, recognizable at the surface of intact hepatitis B virus particles by protecting immunoglobulins. In particular this concerns the group-specific determinant generally indicated by the symbol "a", and which possibly contains several epitopes.

With X and Z are meant the combinations of antigenic determinants found on the HBsAg molecule which differ from the combination represented by A.

X and Z generally encomprise combinations of the so-called type-specific antigenic determinants. In particular these are represented by the combinations classically indicated by the symbols "dw", "dr", "yw" or "yr".

A further subdivision of these type-specific antigenic determinants was proposed by A. M. Couroucé et al. (Develop. biol. Standard, 30, 137–151; 1975). According to this subdivision "yw" can be either "yw$_1$", or "yw$_2$", "yw$_3$" or "yw$_4$", and "dw" can be subdivided into "dw$_2$" and "dw$_4$". Furthermore two subtypes of type "dr" were reported: "drq−" and "drq+" (A. M. Couroucé et al. Vox Sang. 44, 197–211; 1983). All these subtypes belong to the combinations defined by X and Z.

As a consequence according to the invention X and Z can represent for example the set "dw$_4$" and "yr" or the set "dr" and "yw$_1$".

The HBsAg-types which can advantageously be used in the method according to the invention are the sets of combinations "adw" and "ayr", or "adr" and "ayw", wherein of each of the combinations can be used one of the subtypes mentioned above. The one type of such a set is used bound to a solid support, whereas the other type is used bound to a label.

The solid support for HBsAg can be made of any material and may have any form or size enabling separation of the bound and non-bound phases after the incubation in the method according to the invention. HBsAg can be bound directly or indirectly to the support. The direct bond between HBsAg and the solid support may be for example a covalent linkage or an adsorptive bond. The indirect bond between HBsAg and the solid support advantageously may preferably be established via monoclonal or polyclonal antibodies directed against one or more epitopes of HBsAg belonging to the combination represented by X. These antibodies may be covalently or adsorptively bonded to the solid support. Suitable supports are for example test tubes, wells of microtiter strips or plates, rods, spheres, discs manufactured of for example glass, plastics or naturally occuring substances.

A suitable label is any label commonly used in immunoassays, like enzymes, radioactive atoms or substances, fluorescent substances, colored substances, dye sols, sols of metals or metal compounds. The label may have been or be bound directly or indirectly to the HBsAg of the type AZ. Preferably the indirect binding may be established using monoclonal or polyclonal antibodies directed against one or more of the epitopes of HBsAg belonging to the combination represented by Z.

After contacting and incubating the sample to be investigated with the respective HBsAg-AX and HBsAg-AZ reagents, the presence or amount of antibodies protective against HBV infection in the sample is indicated by the formation of insolubilized so-called "Sandwich-complexes" of the type:

$$\text{HBsAg(AX)—anti-HBs—HBsAg(AZ)}.$$

If the HBsAg-AZ reagent used was bonded to the label prior to the incubation the resulting "Sandwich-complex" will also be labeled.

If the HBsAg-Az reagent used in the incubation did not contain a label, the label can be bonded to HBsAg-(Az) either during said incubation or, optionally after a washing step, during a subsequent incubation.

After formation of the labeled "Sandwich-complex" the label can be determined in the immobilized phase or the liquid phase. The method for this determination depends upon the type of label used. If the label is an enzyme a substrate to the enzyme is added to the phase to be tested and conversion of the substrate can be detected by a change in color or color intensity which can be monitored photometrically or visually. If a radioactive atom or substance is used as a label the radiation can be measured from the immobilized or liquid phase.

The sample to be investigated may be incubated in one step with both the HBsAg reagents of the antigenic types represented by AX and AZ, or in successive steps with the respective HBsAg reagents. The successive incubations with the respective HBsAg reagents, optionally with a washing step in between the two incubations, will generally yield the most sensitive method of determination, and therefore constitutes the most preferred method.

The invention also concerns test kits for use with the method according to the invention. These test kits at least contain HBsAg of the type AX bound to a solid support and HBsAg of the type AZ bound to a label; AX and AZ here have the meaning defined before. The test kits may further contain auxiliaries such as buffers, standards (positives and negatives), and materials (in particular chemicals) necessary for the detection of the label. If the label is an enzyme substrate for this enzyme may be included in the test kit; if the label is a sol particular of a dye, metal or metal compound the test kit may contain chemicals to dissolve the label bound to the solid support, in order to enhance the detection.

EXAMPLE 1

A. Preparation of coated solid phase

Hepatitis B surface antigen of subtype ayr (HBsAg-ayr) has been isolated and purified by immune chromatography (L. Kuypers, G. Wolters and A. Schuurs in: Affinity Chromatography and Related Techniques; Proceedings of the 4th International Symposium, Veldhoven, the Netherlands, June 22–26, 1981. Elsevier Scientific Publ. Company).

The wells of polystyrene microtitration plates (Immulon: Greiner, West Germany) were filled with 130 $\mu$l of a solution of HBsAg-ayr (100 ng/ml) in carbonate buffer (0.05 mol/l, pH 9.7) and incubated overnight at 15°–25° C. to coat the surface of the wells with HBsAg-ayr. Plates were emptied, washed with TRIS buffer (0.2 mol/l, pH 7.4) containing 0.5 g/l Tween 20 (polyoxyethylene(20)sorbitan monooleate), dried and stored dry at 2°–8° C. until use.

B. Preparation of marker-complex

Hepatitis B surface antigen of subtype adw (HBsAg-adw) has been isolated from tissue culture of a hepatoma cell line.

Mouse antibodies against the d epitope of HBsAg-adw have been obtained by cell fusion technology. These monoclonal antibodies have been coupled to horseradish peroxidase by the periodate coupling method as described by Wilson et al. (in: Immunofluorescence and Related Staining Techniques ed. Knapp et al. (1978) Elsevier/North-Holland Amsterdam p. 215–224). A suitable complex of HBsAg-adw and monoclonal anti-d labelled with peroxidase was selected by checkerboard titration. The best results were obtained with 1000 ng/ml HBsAg-adw in the complex.

C. Test procedure

A HBsAg-ayr coated plate (prepared according to A) was filled with 100 $\mu$l/well of controls (positives and negatives) and samples or reference preparations. The plate was covered with a seal and incubated overnight at 15°–25° C. Thereafter the fluid in the wells was aspirated and the wells were washed 4 times using 0.3 ml/well of phosphate buffered saline (PBS) containing 0.5 g/l Tween 20.

Subsequently 100 $\mu$l/well of the marker complex prepared according to B was added and incubated for 2 hours at 37° C.

After a second wash step (see supra) 100 $\mu$l/well of substrate to the peroxidase (tetramethylbenzidine/peroxide in an acetate-citrate buffer of pH 6.0) was added (E. Bos et al. (1981) J. Immunoassay 2, 187–204). After incubation during half an hour at 15°–25° C. the enzyme reaction was stopped by adding 100 $\mu$l/well of 2 mol/l $H_2SO_4$. The final light absorption was measured photometrically at 450 nm.

D. Results

Various dilutions of a World Health Organisation (WHO) anti-HBs standard were tested according to the above test procedure.

The sensitivity of the detection method was found to be between 4 and 8 anti-HBs units/l.

EXAMPLE 2

The wells of polystyrene microtitration plates were coated with HBsAg-adw according to the method outlined in 1A.

The marker-complex was prepared from HBsAg-ayr and peroxidase labeled monoclonal antibodies directed against the y-epitope.

The test procedure was as described under 1C.

The sensitivity of this test system was between 8 and 16 WHO anti-HBs units/l.

EXAMPLE 3

Reagents and test procedure were the same as in Example 1, except for the incubation with the sample which was done for 2 hours at 37° C.

The sensitivity was between 8 and 16 WHO anti-HBs units/l.

EXAMPLE 4

The reagents were the same as in Example 1; the test procedure was changed in such a way that the sample and the marker complex were incubated simultaneously in the coated wells overnight at 15°–25° C.

The sensitivity was between 8 and 16 WHO anti-HBs units/l.

EXAMPLE 5

Reagents and test procedure were the same as in Example 4, except for the incubation which was done for 2 hours at 37° C.

The sensitivity was between 16 and 32 WHO anti-HBs units/l.

EXAMPLE 6

A. The wells of polystyrene microtitration plates were coated with HBsAg-ayr using the procedure described in Example 1A.

B. HBsAg-adw was purified by immune chromatography (Example 1A) and coupled to horseradish peroxidase (HRP) using N-succinimidyl 3-(2-pyridyldithio)propionate according to Carlson et al. (Biochem. J. 173, 723–37, 1978), thus obtaining (HBsAg-adw)-HRP conjugate.

C. The test procedure described in Example 1C was used.

D. In this test system were tested:

monoclonal antibodies specific for the d, y, w, r and a determinant of HBsAg.

serum samples from post-acute hepatitis B patients, which had been infected with various HBsAg subtypes.

serum samples from individuals immunized with HBsAg.

serum samples for healthy volunteer donors, free of the known hepatitis B markers.

The results of these tests are given in Table 1.

TABLE 1

| Samples | Absorbance | | | |
|---|---|---|---|---|
| Mouse monoclonal anti-HBsAg, specific for: | | | | |
| d-determinant | 0.311 | | | |
| y-determinant | 0.278 | | | |
| w-determinant | 0.305 | | | |
| r-determinant | 0.289 | | | |
| a-determinant | >2.000 | | | |
| Sera from post-hepatitis B patients infected with: | | | | |
| HB subtype adw | >2.000 | | | |
| HB subtype ayw | >2.000 | | | |
| HB subtype adr | >2.000 | | | |
| HB subtype ayr | >2.000 | | | |
| Individuals immunized with HBsAg | Absorbance from individual no.: | | | |
| | 1 | 2 | 3 | 4 | 5 |
| | >2.000 | >2.000 | 1.817 | 0.763 | 0.679 |
| Healthy volunteer donors | 0.301 | 0.270 | 0.285 | 0.311 | 0.297 |

We claim:

1. A method for the detection or determination of immunoglobulins which provide full protection against hepatitis B infection comprising the steps of:
    (a) providing a given quantity of insolubilized hepatitis B surface antigens of the antigenic type AX, wherein A represents one or more epitopes common to all hepatitis B surface antigen types, and X represents a combination of the epitopes which are not common to all hepatitis B surface antigen types;
    (b) providing a given quantity of labeled hepatitis B surface antigens of the antigenic type AZ, wherein A has the same meaning given above, and Z represents a combination of the epitopes which are not common to all hepatitis B surface antigen types, and wherein said combinations X and Z do not contain any epitopes in common;
    (c) contacting and incubating a sample containing the immunoglobulins to be demonstrated in a liquid medium with the components of steps (a) and (b) to form a reaction mixture having a liquid and a solid phase;
    (d) separating the liquid phase from the solid phase; and
    (e) detecting or determining the labeled component in the liquid and/or the solid phase, which detection or determination is a measure of the presence and/or quantity of said immunoglobulins to be detected or determined.

2. A method according to claim 1, wherein the sample containing the immunoglobulins to be detected or determined is first contacted and incubated in a liquid medium with the insolubilized hepatitis B surface antigens, optionally followed by a washing step, and subsequently followed by contacting and incubating the insolubilized phase with the labeled hepatitis B surface antigens of the antigenic type AZ.

3. A method according to claim 1 wherein the labeling substance is directly coupled to the hepatitis B surface antigens of the antigenic type AZ.

4. A method according to claim 1 wherein the labeling substance is coupled to the hepatitis B surface antigens of the antigenic type AZ by way of antibodies directed against said antigens.

5. A method according to claim 4 wherein the antibodies are polyclonal antibodies directed against epitopes belonging to the combination of epitopes represented by Z.

6. A method according to claim 4 wherein the antibodies are monoclonal antibodies directed against at least one epitope belonging to the combination of epitopes represented by Z.

7. A test kit for the detection or determination of immunoglobulins which provide full protection against hepatitis B infection, comprising:
    (a) a given quantity of insolubilized hepatitis B surface antigens of the antigenic type AX, wherein A represents one or more epitopes common to all hepatitis B surface antigen types, and X represents a combination of the epitopes which are not common to all hepatitis B surface antigen types;
    (b) a given quantity of labeled hepatitis B surface antigens of the antigenic type AZ, wherein A has the same meaning as given before, and Z represents a combination of the epitopes which are not common to all hepatitis B surface antigen types, and wherein said combinations X and Z do not contain any epitopes in common.

8. A test kit according to claim 7, wherein the labelling substance is directly coupled to the hepatitis B surface antigens of the antigenic type AZ.

9. A test kit according to claim 7, wherein the labelling substance is coupled to the hepatitis B surface antigens of the antigenic type AZ by way of antibodies directed against said antigens.

10. A test kit according to claim 9, wherein said antibodies are polyclonal antibodies directed against one or more epitopes belonging to the combination of epitopes represented by Z.

11. A test kit according to claim 9, wherein said antibodies are monoclonal antibodies directed against one or more epitopes belonging to the combination of epitopes represented by Z.

12. A test kit according to claim 7, wherein the hepatitis B surface antigens of the antigenic type AZ are labeled with a label selected from the group consisting of:
    (i) enzymes,
    (ii) radioactive atoms,
    (iii) radioactive substances,
    (iv) fluorescent substances,
    (v) colored substances,
    (vi) dye sols,
    (vii) sols of metals, and
    (viii) sols of metal compounds.

13. A method for the detection or determination of immunoglobulins which provide full protection against hepatitis B infection comprising the steps of:
    (a) providing a given quantity of insolubilized hepatitis B surface antigens of the antigenic type AX, wherein A represents one or more epitopes common to all hepatitis B surface antigen types, and X represents a combination of the epitopes which are not common to all hepatitis B surface antigen types;

(b) providing a given quantity of hepatitis B surface antigens of the antigenic type AZ, wherein A has the some meaning given before, and Z represents a combination of the epitopes which are not common to all hepatitis B surface antigen types, and wherein said combinations X and Z do not contain any epitopes in common;

(c) providing a given quantity of a labeled antibody reactive with one of the epitopes of the combination of epitopes represented by Z;

(d) contacting and incubating a sample containing the immunoglobulins to be demonstrated in a liquid medium with the components of steps (a), (b) and (c) to form a reaction mixture having a liquid and a solid phase;

(e) separating the liquid phase from the solid phase; and (f) detecting or determining the labeled component in the liquid and/or the solid phase; which detection or determination is a measure of the presence and/or quantity of said immunoglobulins to be detected or determined.

14. A method according to claim 13, wherein the sample containing the immunoglobulins to be detected or determined is first contacted and incubated in a liquid medium with the insolubilized hepatitis B surface antigens, optionally followed by a washing step, and subsequently followed by contacting and incubating the insolubilized phase with the hepatitis B surface antigens of the antigenic type AZ and with the detectable compound.

15. A method according to claim 13 wherein the hepatitis B surface antigens of the antigenic type AZ and the detectable compound are contacted and incubated with the insolubilized phase in one single step.

16. A method according to claim 13 wherein the hepatitis B surface antigens of the antigenic type AZ are contacted and incubated with the insolubilized phase in a first step, and subsequently the detectable compound is added and incubated with the insolubilized phase.

17. A method according to claim 13 wherein said antibodies are polyclonal antibodies directed against at least one epitope belonging to the combination of epitopes represented by Z.

18. A method according to claim 13 wherein said antibodies are monoclonal antibodies directed against one or more epitopes belonging to the combination of epitopes represented by Z.

19. A test kit for the detection or determination of immunoglobulins which provide full protection against hepatitis B infection comprising:

(a) a given quantity of insolubilized hepatitis B surface antigens of the antigenic type AX, wherein A represents one or more epitopes common to all hepatitis B surface antigen types, and X represents a combination of the epitopes which are not common to all hepatitis B surface antigen types;

(b) a given quantity of hepatitis B surface antigens of the antigenic type AZ, wherein A has the same meaning given before, and Z represents a combination of the epitopes which are not common to all hepatitis B surface antigen types, and wherein said combinations X and Z do not contain any epitopes in common;

(c) a given quantity of a labeled antibody reactive with one of the epitopes of the combination of epitopes represented by Z.

20. A test kit according to claim 19 wherein the detectable compound comprises a label and one or more antibodies directed against one or more epitopes of the combination of epitopes represented by Z.

21. A test kit according to claim 20 wherein said antibodies are polyclonal antibodies directed against at least one epitope belonging to the combination of epitopes represented by Z.

22. A test kit according to claim 20 wherein said antibodies are monoclonal antibodies directed against one or more epitopes belonging to the combination of epitopes represented by Z.

* * * * *